United States Patent
Fournier

(10) Patent No.: US 9,775,887 B2
(45) Date of Patent: Oct. 3, 2017

(54) ENZYME FORMULATION FOR REDUCING SALICYLATE INTOLERANCE

(71) Applicant: Thea Fournier, North Andover, MA (US)

(72) Inventor: Thea Fournier, North Andover, MA (US)

(*) Notice: Subject to any disclaimer, the term of this patent is extended or adjusted under 35 U.S.C. 154(b) by 0 days.

(21) Appl. No.: 14/967,746

(22) Filed: Dec. 14, 2015

(65) Prior Publication Data

US 2017/0165329 A1 Jun. 15, 2017

(51) Int. Cl.
  *A61K 38/43* (2006.01)
  *A61K 38/48* (2006.01)
  *A61K 38/46* (2006.01)
  *A61K 38/47* (2006.01)

(52) U.S. Cl.
  CPC ........ *A61K 38/4826* (2013.01); *A61K 38/465* (2013.01); *A61K 38/47* (2013.01); *C12Y 301/03* (2013.01); *C12Y 302/01* (2013.01); *C12Y 302/01026* (2013.01); *C12Y 302/01108* (2013.01); *C12Y 304/21001* (2013.01)

(58) Field of Classification Search
  None
  See application file for complete search history.

(56) References Cited

PUBLICATIONS

Hare L. et al. Dietary Salicylates. J Clinical Path 56:649-650, 2003.*
Houston Enzymes Newsletter. The Enzyme Digest Issue 35, Sep. 2010, pp. 1-4.*
http://www.kirmangroup.com/phenol-assist-enzyme.html Product page for Phenol Assist(TM) unknown date.*
Houston Enzymes No-Fenol product page, supplement facts.*
Dr. Tennant's Digest Enzyme Formula product page, Supplement Facts, Jun. 2014.*

* cited by examiner

*Primary Examiner* — Ralph Gitomer
(74) *Attorney, Agent, or Firm* — Eric P. Mirabel

(57) ABSTRACT

Disclosed is a formulation of the following enzymes: Beta Glucanase, Chymotrypsin, Phytase, Lactase, and Invertase, which has been found to be effective in treating salicylate intolerant people, and causing a significant improvement in a wide variety of pathologies and symptoms, including, but not limited to: stuttering, migraines, ADHD, behavioral deficits, Tourettes disease, seizures, autism (ASD), atrial fibrillation, anxiety, depression, joint pain, cognitive and perceptual disorders, respiratory difficulties and non-diabetic neuropathy.

5 Claims, No Drawings

ENZYME FORMULATION FOR REDUCING SALICYLATE INTOLERANCE

BACKGROUND

Many people suffer from food intolerance. It is believed that many such people's intolerances can be traced to use of pesticides, and/or genetically engineered foods, which adversely affect liver pathways, inhibit enzymes, and disrupt amino acids in the body which ultimately can lead to food intolerances.

Intolerance to gluten has been widely discussed. Less well known, but equally widespread, is intolerance to salicylates and histamines. Salicylates are compounds that are manufactured synthetically and found in artificial colorings and flavorings, solvents, many personal care products and elsewhere in some foods as additives/preservatives. These salicylate compounds are also naturally occurring in many plant foods, including fruits, vegetables, and herbs/spices. In the course of many years of consulting and observing thousands of clients, the inventor has found that patients who follow the recommended dietary restrictions (which reduce or substantially eliminate salicylates), experience a significant improvement in a wide range of symptoms and pathologies. Eliminating salicylates and adhering to the recommendations, appears to be highly effective in treating a wide range of symptoms/conditions, including, but not limited to: stuttering, migraines, ADHD, behavioral deficits, Tourettes disease, seizures, autism (ASD), atrial fibrillation, anxiety, depression, joint pain, cognitive and perceptual disorders, respiratory difficulties and non-diabetic neuropathy.

SUMMARY

A formulation of the following enzymes: Beta Glucanase, Chymotrypsin, Phytase, Lactase, and Invertase, has been found to be effective in treating salicylate intolerant people, and causing a significant improvement in a wide variety of symptoms/conditions, including, but not limited to: stuttering, migraines, ADHD, behavioral deficits, Tourettes disease, seizures, autism (ASD), atrial fibrillation, anxiety, depression, joint pain, cognitive and perceptual disorders, respiratory difficulties and non-diabetic neuropathy. It is believed that the formulation catalyzes breakdown of salicylate compounds in vivo.

More particularly, the preferred dosages of the enzymes in the formulation are as follows: Beta Glucanase: 200 BGU; Chymotrypsin (from porcine, preferably, or beef) 3.0 mg (and not less than 3000 USP units); Phytase 30 FTU; Lactase 600 ALU, and Invertase 600 INVU. More preferred, is ingesting two or more of the formulation with the foregoing contents with each meal. A preferred carrier for the formulation is a vegetable capsule (including, mostly cellulose and distilled water). Most preferred is that the formulation be free of any of the following: casein, gluten, dairy, egg, soy, corn, peanuts, tree nuts, and fish.

A discussion of testing and demonstrating the safety and efficacy of the formulation is set forth below in the Detailed Description.

DETAILED DESCRIPTION

It has been found over decades of study, that people who adopt a dietary restriction plan which eliminates foods and food products containing salicylates experience significant improvement in some, but not limited to, the following symptoms and conditions: stuttering, migraines, ADHD, behavioral deficits, Tourettes disease, seizures, autism (ASD), atrial fibrillation, anxiety, depression, joint pain, cognitive and perceptual disorders, respiratory difficulties and non-diabetic neuropathy. The formulation will be administered to two groups of patients in order to test its treatment effects.

Group/Branch One:

After baseline symptom information has been collected, patients in group one will remove salicylates 100% from their daily diet for two months. After the two months, they will fill out the form again checking symptoms they are experiencing and severity of them. The Formulation will then be administered to each patient who has experienced significant improvement in those symptoms/conditions. After three weeks on the formulation, patients will begin consuming salicylate containing food. Their symptoms will be monitored bi-weekly for two months. As a result of being on the Formulation, it will be determined if they can successfully eat salicylates without a recurrence of adverse symptoms, if there is increased improvement, or if symptoms worsen.

Group/Branch Two:

Salicylate intolerant patients in group two will remove no salicylates from their daily diet. Eligible patients will be randomly assigned to receive the Formulation (n=25) or Placebo (n=25) after eligibility is established and baseline symptoms and severity of symptoms have been assessed. Over a two month period of follow-up, patients symptoms and conditions will be monitored at monthly visits. All primary analyses will be based on the intention-to-treat principle. Formulation and placebo groups will be compared and proof of efficacy would be a statistically significant improvement in one or more of the foregoing of symptoms or conditions. Statistically significant differences at the alpha 0.05 level will be reported.

The preferred dosages of the enzymes set forth in the Summary are not the only dosages possible, and other more optimal dosages and dosing regimes may be discovered with routine experimentation, now that the preferred dosages are known. The routine experimentation would involve providing different dosages under different regimes, using behavioral kinesiology to determine the appropriate dosage and optimal regime for each individual child or adult in the case study, and determining which patients improved most in their monitored diseases and conditions.

The starting point for determining optimal dosing and an optimal regime, is the preferred dosages, administered once a day, as above. Variations could be doubling, halving, or otherwise and reducing the quantities of one or more of the enzymes in a formulation. The dosing regime modifications could include increasing or reducing the number of administrations of the formulation each day for patients in a particular group. Such experimentation is routine in the pharmaceutical industry.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for treating symptoms of one or more of the following diseases or conditions: stuttering, diabetes-associated neuropathy, migraines, ADHD, Tourette's disease, seizures, autism and atrial fibrillation, comprising administering a formulation consisting essentially of the enzymes: Beta Glucanase, Chymotrypsin, Phytase, Lactase and Invertase.

2. The method of claim 1 wherein the quantities of the enzymes in the formulation are: Beta Glucanase, 200 BGU; Chymotrypsin, not less than 3000 USP units; Phytase 30 FTU; Lactase 600 ALU and Invertase 600 INVU.

3. The method of claim 2 wherein the Chymotrypsin is derived from porcine or beef and the quantity is 3.0 mg.

4. The method of claim 1 wherein the diseases or conditions are ADHD and migraines.

5. The method of claim 1 wherein the formulation is administered at least once per day.

* * * * *